(12) United States Patent
Chu et al.

(10) Patent No.: US 9,095,323 B2
(45) Date of Patent: Aug. 4, 2015

(54) HOLDER REMOVABLY MOUNTABLE ON ASSOCIATED DEVICE

(75) Inventors: Jennifer Chu, Haverford, PA (US); Janette Chu, Broomall, PA (US)

(73) Assignee: JusJas LLC, Haverford, PA (US)

( * ) Notice: Subject to any disclaimer, the term of this patent is extended or adjusted under 35 U.S.C. 154(b) by 674 days.

(21) Appl. No.: 13/436,221

(22) Filed: Mar. 30, 2012

(65) Prior Publication Data

US 2012/0253436 A1    Oct. 4, 2012

Related U.S. Application Data

(60) Provisional application No. 61/470,778, filed on Apr. 1, 2011.

(51) Int. Cl.
  *A61B 19/02* (2006.01)
  *A61N 1/04* (2006.01)
  *A61N 1/36* (2006.01)

(52) U.S. Cl.
  CPC ........... *A61B 19/0256* (2013.01); *A61N 1/0452* (2013.01); *A61N 1/0456* (2013.01); *A61N 1/0472* (2013.01); *A61N 1/36014* (2013.01)

(58) Field of Classification Search
  CPC ............. A61B 19/0256; A61N 1/0452; A61N 1/36014; A61N 1/0472; A61N 1/0456
  USPC ................ 607/115, 150; 600/393; 248/309.1, 248/316.8, 322, 301; 211/126.8, 85.13; 206/335, 349, 363, 368–370; 433/77; 269/16
  See application file for complete search history.

(56) References Cited

U.S. PATENT DOCUMENTS

| | | |
|---|---|---|
| 3,254,817 A | 6/1966 | Bartz |
| D263,624 S | 3/1982 | Stenzler et al. |
| D324,735 S | 3/1992 | Collister et al. |
| 6,298,793 B1 | 10/2001 | Turner et al. |
| D492,113 S | 6/2004 | Bayer et al. |
| D508,774 S | 8/2005 | McAndrew |
| D510,770 S | 10/2005 | Emerson |
| 7,207,438 B2 | 4/2007 | Lieffring et al. |
| 7,264,084 B1 | 9/2007 | Switzer |
| 7,354,023 B1 | 4/2008 | Wappler |
| 7,364,040 B1 | 4/2008 | Hunter et al. |
| 7,374,018 B1 | 5/2008 | Thrun |
| D585,647 S | 2/2009 | Whiteside et al. |
| 7,526,972 B2 | 5/2009 | Stevens |
| D595,782 S | 7/2009 | Whitfield |
| D602,256 S | 10/2009 | Johnson |
| 7,669,829 B2 | 3/2010 | Ogatsu |
| 7,725,193 B1 | 5/2010 | Chu |
| 7,854,321 B2 | 12/2010 | Twig et al. |
| 7,877,152 B2 | 1/2011 | Chu |
| D655,410 S | 3/2012 | Chu et al. |
| 2010/0256722 A1 | 10/2010 | Chu |

*Primary Examiner* — Mark W Bockelman
(74) *Attorney, Agent, or Firm* — Banner & Witcoff, Ltd.

(57) ABSTRACT

A holder serves as a removable accessory to a stimulator unit chassis or cabinet, or other device. It can function as an integral part of the device that closely fits over the top of the device, to provide a support for a hand-held tool associated with the device, e.g., a bipolar probe with widely spaced electrodes. The holder, which may be constructed to be of one piece, is configured to be easily removed from the device to facilitate cleaning of the holder and/or to facilitate packing of the stimulator unit (or other device) for shipping purposes, e.g., in case of device repairs, etc. In other embodiments, the holder may associate a tray or box for storing a variety of items with a host device on which the holder is mounted.

4 Claims, 5 Drawing Sheets

HOLDER REMOVABLY MOUNTABLE ON ASSOCIATED DEVICE

CROSS-REFERENCE TO RELATED APPLICATION

This application claims priority to U.S. provisional application Ser. No. 61/470,778, filed Apr. 1, 2011, the contents of which is hereby incorporated in its entirety, bodily and by reference.

BACKGROUND

Bipolar stimulator probes attachable to an electrical stimulator device or an electromyographic (EMG) device are commercially available for surface stimulation of peripheral nerves of the human body. Such apparatus provide both a stimulation electrode and a reference electrode on a single device.

These types of devices can be used in surface stimulation for eliciting muscle twitches of the type sought in a muscle pain and discomfort relieving method developed by the present inventor, referred to as Surface Applied Electrical Twitch Obtaining Intramuscular Stimulation. This methodology is described in the U.S. Pat. No. 7,725,193 to present inventor Dr. Jennifer Chu. Treatments utilizing the methodology are clinically offered by Dr. Chu, and assignee JusJas, LLC, under the service mark eToims®. For convenience, this service mark will be used herein to refer to this methodology as offered by the inventor and/or JusJas, LLC or its affiliates. This technique involves the provision of brief electrical stimulation at multiple motor end-plate zones in many muscles.

The performance of eToims® using a bipolar probe with widely spaced electrodes developed by the present inventor is described in U.S. Pat. No. 7,877,152, hereby incorporated by reference in its entirety. A subsequent generation of the tool, and composite conductive pads/plugs for the same, are shown and described in the present inventor Dr. Jennifer Chu's U.S. application Ser. No. 12/625,667, published under No. 2010/0256722, also hereby incorporated by reference in its entirety.

There is a need for a holding/resting system for the bipolar probe with widely spaced electrodes, where the probe can be placed during or after a session of use. This would facilitate keeping the electrodes sanitary for the Surface Applied Electrical Twitch Obtaining Intramuscular Stimulation procedure. This is especially important since the electrodes (e.g., composite pads/plugs as disclosed in aforementioned U.S. application publication No. 2010/0256722) are, in use, typically wetted and there is no place to lay down the probe during a treatment session without contaminating the table or cart surface on which the stimulator device rests.

Since the electrodes are wet, the probe cannot be placed on top of the electrical stimulator device (e.g., eToims® ET127 stimulator unit available from eToims® Medical Technology, LLC of Philadelphia Pa.); doing so could cause water ingress into the device and create a shock hazard, as well as potentially damage the device.

In addition, even if the electrodes are dry, when the front of the device is tilted up using two front legs provided on the device (this allows the clinician to have a better view of the front panel), there is tendency for the probe to slide off the top surface. On the other hand, a separate stand-alone holder can easily be displaced or tumble over, fall off a utility cart upon which it is placed with the stimulator device, and/or can be simply lost or misplaced.

BRIEF SUMMARY OF SELECTED INVENTIVE ASPECTS

To deal with these issues, in an aspect, the present invention provides a probe holder as a removable accessory to the stimulator device chassis or cabinet. It can, in an embodiment, function as an integral part of the device that closely fits over the top of the device. In accordance with a further aspect, the probe holder, which may be constructed to be of one piece, is configured to be easily removed from the device to facilitate cleaning of the probe holder and/or to facilitate packing of the ET127 stimulator unit (or other device) back into its original foam packaging for shipping purposes, e.g., in case of device repairs, etc.

DETAILED DESCRIPTION OF EXAMPLE EMBODIMENTS

Figure 1:
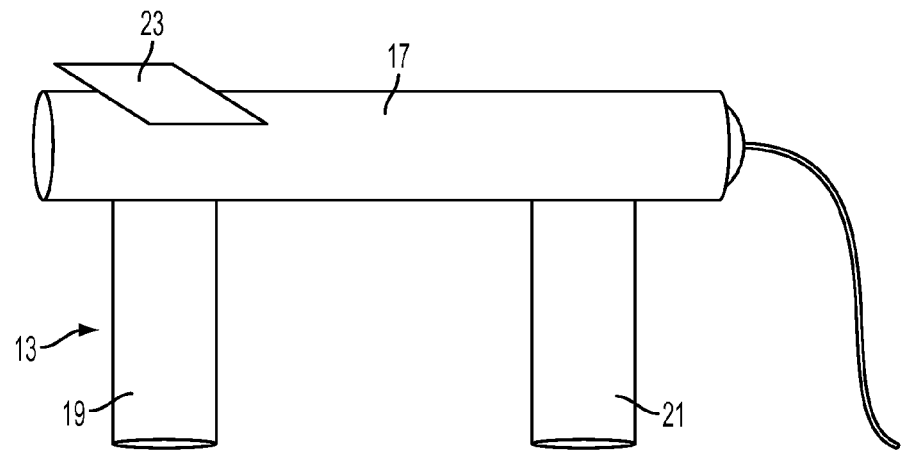
FIG. 1 is a simplified diagrammatic depiction of a bipolar probe with widely spaced electrodes, a type of tool that may be supported by a holder according to an embodiment of the present invention.

An exemplary embodiment, particularly well suited for use with a bipolar stimulator probe of the type disclosed in U.S. patent application publication No. 2010/02567221, is illustrated in the accompanying drawing Figures. As shown, the holder 1 provides a tool cradle 3 comprising two spaced members 5, 7 each having a U-shaped trough 9, 11. The two troughs are provided in axial alignment with each other for reception of the tool 13 (see FIGS. 1 and 3) lengthwise along the axis, alongside the chassis or cabinet 15 of the ET127 stimulator unit (or other device) to which the holder is shown mounted. Additionally, the distance between the two troughs 9, 11 is preferably sufficient to allow the connecting part 17 of the probe 13 between the widely spaced probe legs 19, 21 to fit well without the mouths of the troughs catching on the control panel 23 on top of the probe, or the wet or dry electrodes 24 (see FIG. 3) placed in the distal ends of the probe legs 19, 21. In the embodiment shown, the spaced members 5, 7 are positioned such that the probe legs 19, 21 will straddle the two spaced members on opposite outer sides. In other embodiments, the spacing of the supporting members could be made larger or smaller so as to optimally support various tool types and configurations.

Figure 2:
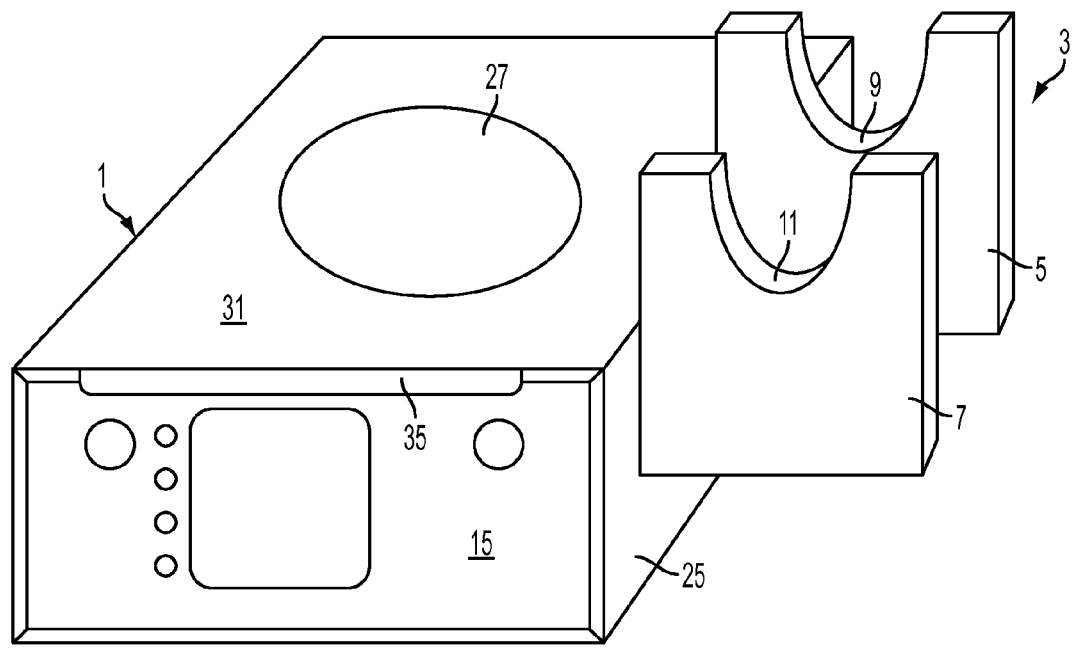
FIG. 2 is a front-side elevation view of an electrical stimulator unit used in conjunction with the bipolar probe tool depicted in FIG. 1, and having installed thereon a holder according to an embodiment of the present invention.
Figure 3:
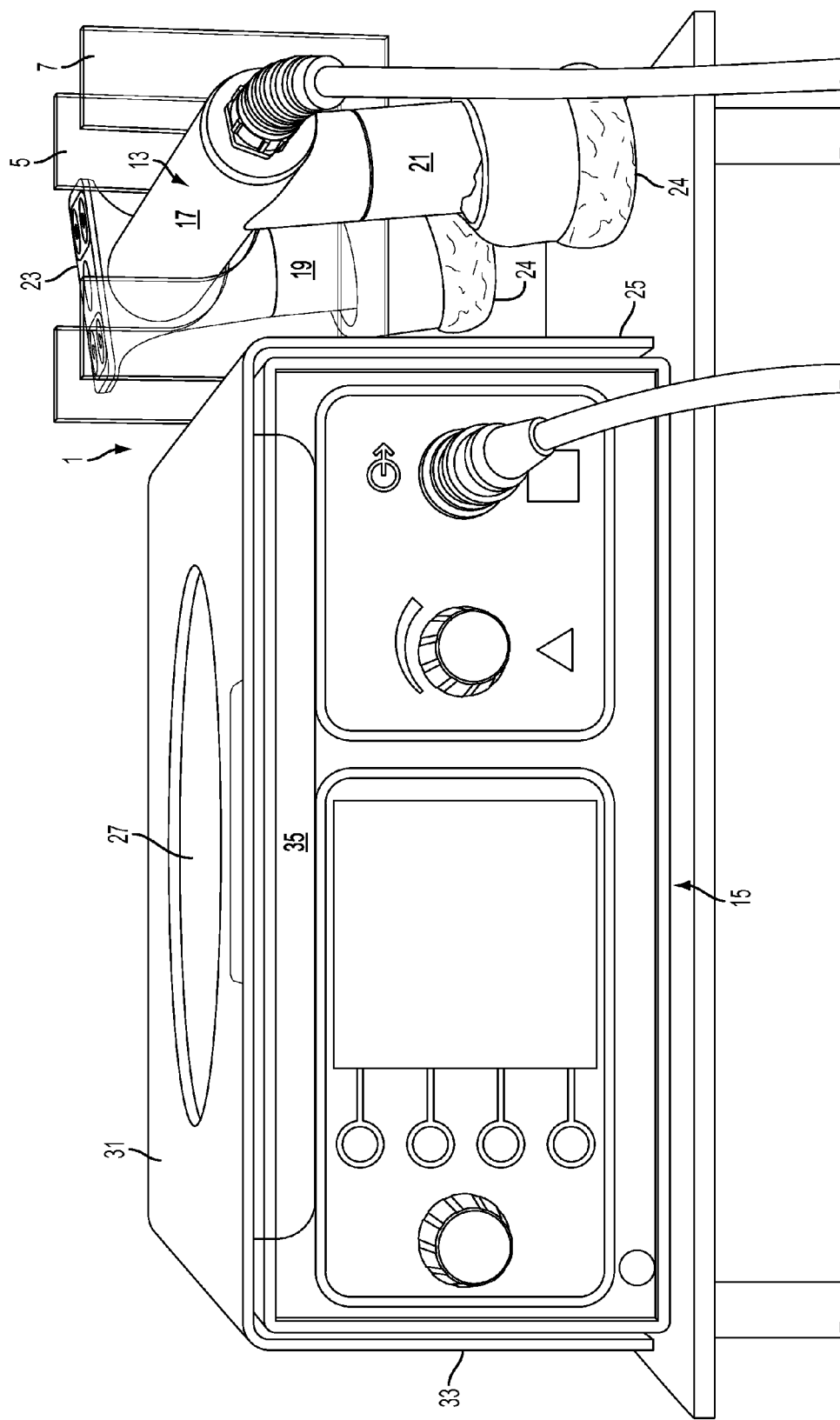
FIG. 3 is a further front-side elevation view of an electrical stimulator unit used in conjunction with a bipolar probe tool of the general type depicted in FIG. 2, having installed thereon a holder as seen in FIG. 2, and further showing the bipolar probe to resting in a cradle of the holder.
Figure 4:
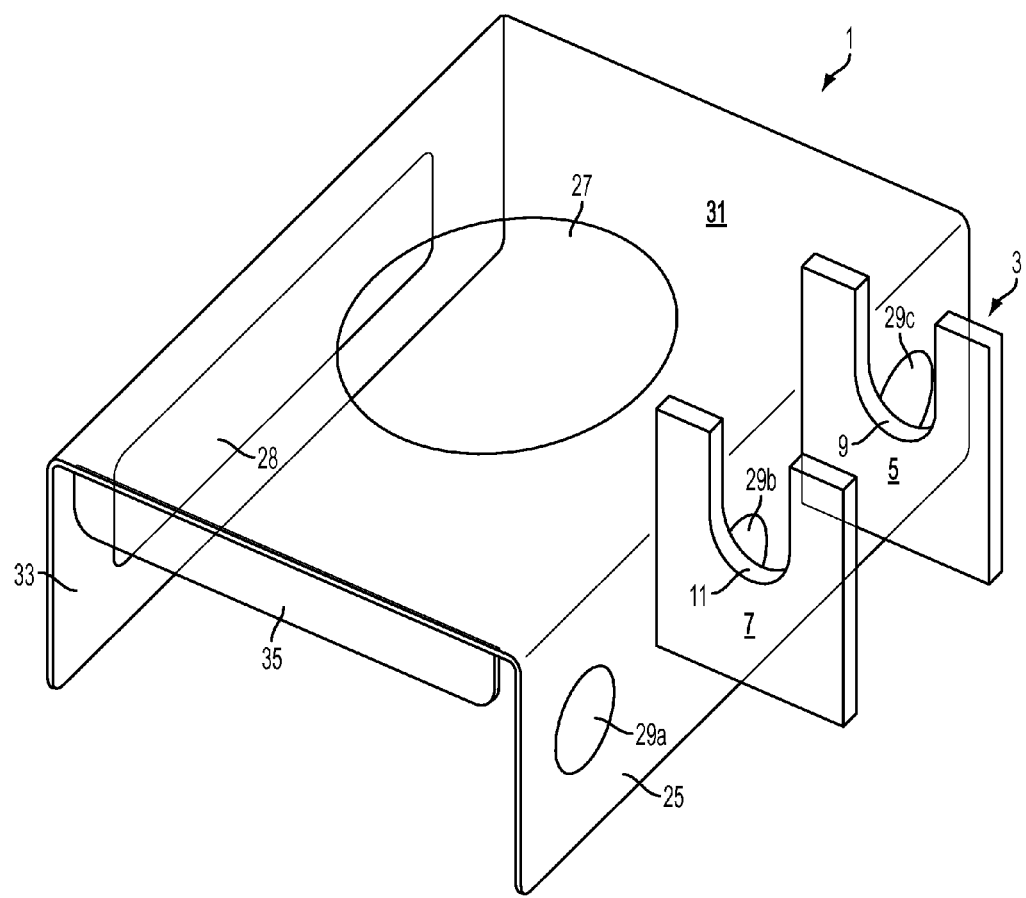
FIG. 4 is a perspective view of the holder of FIGS. 2 and 3, shown by itself.
Figure 5:
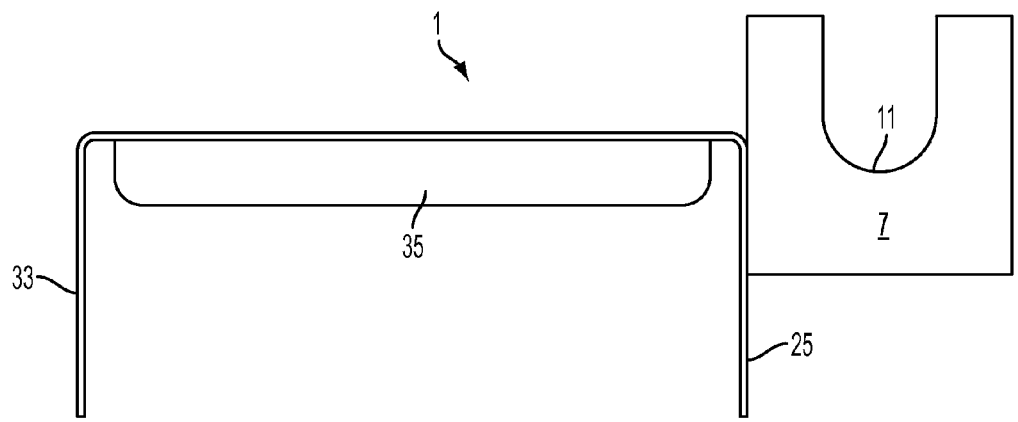
FIG. 5 is a front elevation view of the holder.
Figure 6:
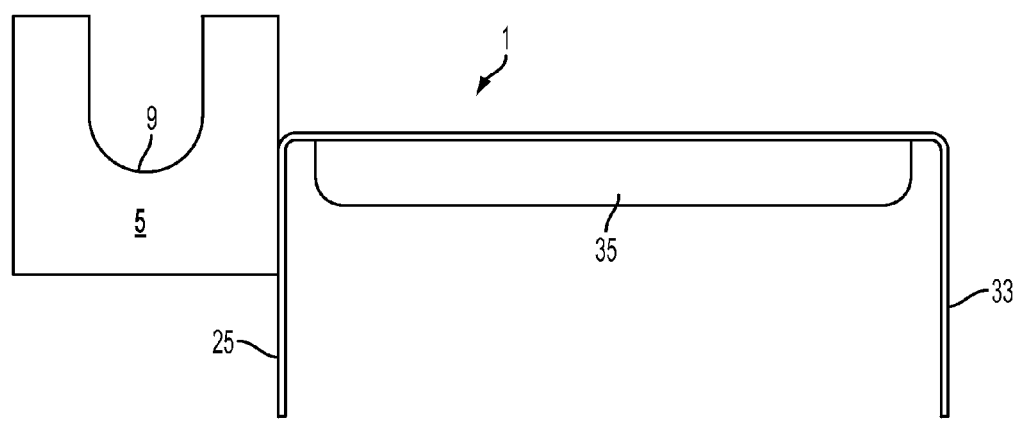
FIG. 6 is a rear elevation view of the holder.
Figure 7:
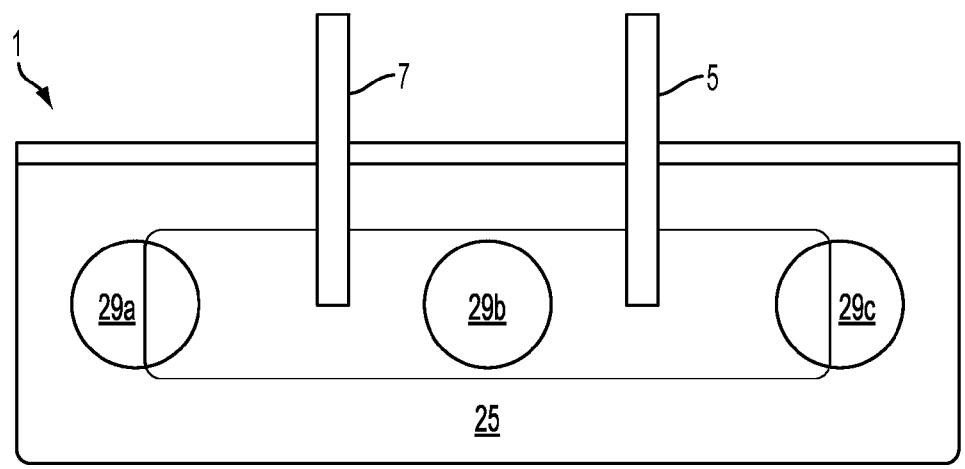
FIG. 7 is a right side elevation view of the holder.
Figure 8:
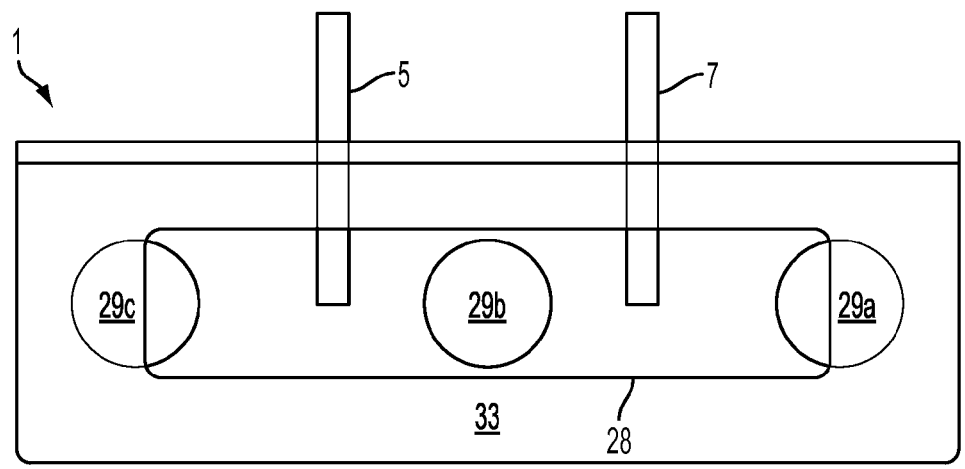
FIG. 8 is a left side elevation view of the holder.

In an exemplary embodiment shown in FIGS. 3-8, the entire probe holder 1 is made of clear acrylic plate or sheet material. Such material is desirable for its transparency, strength and durability, as well as cleanability/chemical resistance, and its general inhospitality to bacterial colonization. FIGS. 4-8 show the holder by itself, while FIGS. 2 and 3 show it mounted on an ET127 stimulator and having the hand-held bi-polar electrical stimulation probe tool 13 supported in the cradle 3. The probe tool 13 shown is equipped, at the distal ends of its two legs, with electrode pads 24 that may be wetted, as previously described. As can be seen, these distal leg ends/electrodes are supported by the holder 1 above the underlying surface upon which the ET127 unit rests.

The protruding off-set cradle 3, which comprises the two spaced members 5, 7 (and optionally a base plate or other connecting structure extending in between the two members), may be adhered to the side panel of the probe holder with acrylic cement. In a process termed "solvent welding," the cement softens the acrylic surfaces so they become merged—molecules intertwine and the separate pieces become joined as one integral piece.

All surfaces or curves of the cradle and troughs are preferably rounded off to avoid cutting or scratching the operator who will place the probe 13 in the cradle 3 and remove it from the cradle for use. The troughs 9, 11 are preferably sufficiently spaced away from the side panel 25 so that even a large man's hand is able to grab hold of the connecting bridge of the probe tool between the probe legs.

For use with the aforesaid bipolar stimulator probe tool 13, the cradle 3 ought to be set sufficiently high against the side of the ET127 (or other) stimulator device so that the electrodes will not contaminate the supporting surface upon which ET127 rests upon. With the probe tool 13 held in the cradle 3, there should be sufficient space under the probe's electrodes so that the electrodes will stay clear of the surface supporting the device. (Such an arrangement is shown in FIG. 3, as previously described.) Preferably, there will be enough room for placement of a dripping pan/tray to collect any excess water that may drip from the electrodes (if the need arises).

There is heat emission from an electrical stimulator such as the ET127, when that unit 15 is in operation. To avoid overheating, that heat emission should not be substantially impeded. In the illustrated embodiment, heat escape from the ET127 (or other) device upon which the tool holder 1 is mounted is allowed by openings 27, 28, 29a, 29b and 29c cut or otherwise formed in the top panel 31 and the two side panels 25, 33 of the probe holder. In the illustrated probe holder embodiment, the holder top panel 31 spans the entire top surface of the device (except for the area of the opening), and the side panels 25, 33 drop down from the top panel 31 perpendicularly on opposite sides, parallel to and in contact with the side panels of the device's outer cabinet. Overall, the cabinet engaging structure of the holder 1 has an open-ended, open bottom inverted U-shape in cross-section. The open ends leave fully unimpeded access to connections and controls that may be provided at the rear and front faces of the electronic device 15 to which it is mounted. A down-turned lip 35 (which may be jointed or in one piece with the top and side panels) may be provided extending down from top panel 31 at one or both ends, to further assist in properly installing and retaining the holder 1 on the ET127 (or other) device. The deep side panels 25 and 33, and their close fitting to the electronics device cabinet 15, provide stability to the cradle 3 and prevent it from tipping over. Resistance to tipping may be achieved notwithstanding the moment generated by the off-set cradle that must bear the weight of the probe 13 suspended within it.

In a further aspect, the probe holder 1 itself can be made portable by making it with a joint or hinge between the side panels 25, 33 and the top panel 31. This gives the ability to fold the left side panel 33 over onto the top panel 31, and the right side panel 25 supporting the cradle 3 may be folded under the top panel, to make the holder more compact and convenient for easy packing Such a probe holder (or holder for other items) is user-friendly in that it may be unfolded and easily installed for use by slipping onto the associated base device, etc., with no additional assembly required.

In a broader aspect, the present inventive holder is not limited to one for holding an electrical probe tool. The same concept can be applied and adapted to fit various other hand-held tools used in other types of trade, technology or in the kitchen. In one variation, the cradle may instead be a solid piece or other structure forming a tray or side-box that could be used for placing small tools or gadgets that are frequently used but which can be easily lost or misplaced, such as pens, brushes, watches, jewelry etc. In such instances, the holder could be configured to fit over the top of an associated cabinet, chassis box, etc., similar to the manner in which the illustrated probe holder is removably mounted on an electronics unit cabinet/chassis. The probe holder with its cradle/tray/side-box can be made of various materials such as wood, metal, rubber or other types of plastic or foam. A benefit of the holder is that it is structurally associated with a related device or storage structure (e.g., a cosmetics container) but yet remains easily removable therefrom so that it does not permanently add extra dimensions to the size of the original device/container, or otherwise alter it.

It will be understood that while the invention has been described in conjunction with various embodiments and details thereof, the foregoing description and examples are intended to illustrate, but not limit the scope of the invention. Numerous other variations and arrangements are within the scope of the invention as defined in the appended claims.

The invention claimed is:

1. In combination, an electronic device housed within a cabinet, a hand-held device electrically connectible to said electronic device, and a holder for removably holding said hand-held device in association with said electronic device, said holder comprising:
   a device engaging structure, said structure including a top panel and a pair of spaced side panels depending therefrom, for fitting onto said cabinet; and
   a support member attached to and off-set from said device engaging structure, said support member being capable of supporting said hand-held device above and in spaced relationship to an underlying surface;
   wherein said electronic device is an electrical stimulation unit, said hand-held device is a bipolar stimulation tool with a pair of legs mounting spaced electrodes, and said support member comprises two spaced members positioned to support the stimulation tool with its spaced electrodes spaced above said underlying surface.

2. A combination according to claim 1, wherein each of the two spaced members has a U-shaped trough, the two troughs being provided in axial alignment with each other for reception of the stimulation tool lengthwise along the axis of alignment, alongside said electrical stimulation unit to which the holder is mountable.

3. A combination according to claim 2, wherein the two spaced members are positioned such that when the stimulation tool is supported by the support member the tool's legs straddle the two spaced members on opposite outer sides.

4. A combination according to claim 1, wherein said cabinet has a generally rectangular shape, the top panel spans a top surface of the cabinet, and the side panels drop down from the top panel perpendicularly on opposite sides of the cabinet, parallel to and in contact with corresponding side panels of said cabinet.

* * * * *